United States Patent

Pringle

[11] 4,281,663
[45] Aug. 4, 1981

[54] PHYSICAL FITNESS INDICATOR

[76] Inventor: Robert D. Pringle, 28a Murrayfield Road, Edinburgh EH12 6ER, Scotland, Scotland

[21] Appl. No.: 40,908

[22] Filed: May 21, 1979

[30] Foreign Application Priority Data

May 26, 1978 [GB] United Kingdom ............... 23217/78

[51] Int. Cl.³ .............................................. A61B 5/02
[52] U.S. Cl. .................................... 128/689; 128/707
[58] Field of Search ............... 128/689, 690, 706, 707, 128/702, 905

[56] References Cited

U.S. PATENT DOCUMENTS

| | | | |
|---|---|---|---|
| 3,518,983 | 7/1970 | Jorgensen | 128/702 |
| 3,575,162 | 4/1971 | Gaarder | 128/905 |
| 3,633,569 | 1/1972 | Brayshaw et al. | 128/702 |
| 3,802,698 | 4/1974 | Burian et al. | 128/707 |
| 4,052,979 | 10/1977 | Scherr et al. | 128/690 |
| 4,129,124 | 12/1978 | Thalmann | 128/690 |
| 4,129,125 | 12/1978 | Lester et al. | 128/702 |

Primary Examiner—William E. Kamm
Attorney, Agent, or Firm—Gerald J. Ferguson, Jr.; Joseph J. Baker

[57] ABSTRACT

A device for indicating the reaction of pulse rate to exercise. In preferred forms, the device measures the pulse rate at rest ($R_1$), the elevated pulse rate ($R_2$) resulting from the performance of a specified amount of work, and the recovery pulse rate ($R_3$) at a specific time after ceasing exertion. The device includes calculating means for directly calculating a fitness index from the three pulse rates according to a chosen one of various formulae. The device also provides a visual or audible pulse output as a timing signal for performing the specified exercise.

15 Claims, 9 Drawing Figures

PHYSICAL FITNESS INDICATOR

This invention relates to an electronic physiological performance testing device.

Research on the measurement of physiological performance capability has shown that the measurement of pulse rate (heart beat rate) under three conditions is relevant to an assessment of the subject's capacity for performing mechanical work. These conditions are:

1. Normal or initial pulse rate ($R_1$)—i.e., the pulse rate at rest.
2. Elevated pulse rate ($R_2$), resulting from the performance of a specific amount of work at a specific rate measured at the end of the period of exertion.
3. Pulse rate after "recovery" ($R_3$)—i.e., the pulse rate measured at a specific time after cessation of exertion.

A simple test (sometimes called the Harvard or Tecumseh step test) has been widely used for assessing performance or fitness in a wide range of military, medical, athletic and industrial situations. This test is based on only one pulse measurement under condition 3 above. The subject is made to step up onto and down from a step of a prescribed height (say 8 inches) at a given rate (say every 2.5 seconds) for a prescribed time (say 3 minutes). The subject then rests for a prescribed time (say 1 minute) at the end of which the pulse rate is measured. The main difficulties are of ensuring a constant rate of stepping (stop watches and metronomes are used to assist this) and of taking account of the individual differences in initial pulse rate and the degree of elevation produced by the exertion (all that seems to be done in this context is to scale the pulse rates measured against a general trend of initial pulse rate variation with age and sex). Notwithstanding these difficulties, however, several major medical surveys have been conducted using this simple test or some variation of it and it seems to be well established.

The invention is based on the fact that the physiological performance of subjects could be much more accurately assessed if all 3 of the above pulse rates could be recorded. Even recording 2 of them would permit a significant improvement. The object of the invention is to provide means whereby the rates can be electronically processed to provide a "performance factor" which permits the basic idea of the above test to be used in a way which eliminates the variations due to the individual differences in initial pulse rate and degree of elevation caused by the exertion.

It is known that athletes and their trainers certainly measure their elevated pulse rates and time their recovery but so far as can be ascertained the only electronic devices available are simple pulse counters which are sometimes used in conjunction with small tape recorders to monitor pulse rate during exertion over a period of time.

According to the invention an electronic physiological performance testing device constructed as a self-contained unit comprises means for receiving signals respresenting pulse rates, means for storing such pulse rates at instants separated in time by a predetermined period, and means for displaying at least one result of such storage. Very advantageously the device may be arranged to compute a performance factor and display the result of the computation.

The device can advantageously be arranged so that it enables:

1. Measurement and storage of pulse rates under at least 2 of the conditions described above.
2. Accurate timing of the intervals and particularly timing of the rate of stepping (one of the more difficult aspects of the simple test as hitherto employed).
3. Processing of the 2 or 3 pulse rates to produce one or more "performance factor(s)" indicating the state of fitness or capacity of the subject.

The device has a range of applications including:

Athletes measuring their capacity at intervals during their own training programme.

Trainers measuring the performance of groups of athletes undergoing the same training programme.

Patients convalescing after coronary or other illness.

Patients undergoing treatment with drugs.

Insurance companies testing prospective life insurance policy holders.

The device extends the range of applications of this type of test beyond the present range of medical and athletic tests because it enables an individual to conduct the test himself consistently and because it provides scope for the elimination of most of the imponderables in the test as hitherto employed.

The device may take the form of a plastic package closely resembling an electronic calculator, having a numeric display and being powered by internal batteries (rechargeable or expendable). In addition there is a pulse sensor with suitable means of attachment to the subject and connection to the device. This may take the form of a piezoelectric displacement sensor (basically similar to a crystal phonograph pick-up) attached to the wrist, throat or ear-lobe and connected to the device by means of a flexible co-axial (screened) lead. The device can be clipped to the breast pocket, hung from the neck or strapped to the wrist—the position of the numeric display being appropriately chosen to be readily visible to the subject during the stepping. It is technologically feasible to reduce the circuitry sufficiently to house the whole device including the pulse sensor in a watch-type case with the sensor bearing on the radial pulse.

The device is preferably provided with means for generating a periodic signal (visual, audible, or both) throughout the stepping time to indicate the rate at which this exercise is to be performed.

In use, the sensor is attached to the subject and the device switched on. The display then shows the initial pulse rate ($R_1$) apparently immediately (actually after a delay of a fraction of a second) and then commences to flash a signal at the rate required for the stepping (typically 2.5 second intervals). This important timing can be indicated by a separate indicator lamp but alternatively can be effected by making some chosen combination of the segments of the display flash at the required rate. It is a desirable addition to provide an audible indication of the stepping rate. This timing signal continues for the duration of the exertion period the end of which is indicated by the display showing the second pulse rate ($R_2$). The subject then rests until the third pulse rate ($R_3$) appears on the display. After this the performance factor is computed and displayed automatically. Alternatively the performance factor can be preselected before the start of the test. A switch can advantageously be provided to operate only the simple pulse measurement part of the program so that the device can be used for straightforward pulse measurement as well as performance assessment.

A most useful performance factor is the following:

$$(R_2-R_3)/(R_2-R_1)$$

The degree of elevation of the pulse rate appears to be a measure of the capacity as well as the condition of the subject whereas the degree of recovery seems to be substantially dependent on the condition of the subject. The above factor therefore takes account of both of these considerations by presenting the recovery as a proportion of the elevation. In a fit subject this performance would be close to one because, whatever the degree of elevation produced in the exertion period, most will be recovered in the rest period. In an unfit subject however, the factor would be very much smaller than one because the degree of elevation will be high and the recovery will only be a very small fraction of the elevation. Thus, without introducing too much elaboration a factor can be computed which relates the degree of recovery to the degree of elevation. It is anticipated that this would be most generally useful as an assessment of the general state of health or fitness of the subject, normalising out (in statistical terms) the random differences in capacity from subject to subject. However, other (more elaborate) formulae may be devised for special applications.

It will be apparent that even with one formula alone the test can be applied to a wide range of applications since the amount of effort can be adjusted to suit the group among which the comparative assessment is to be made. The most obvious way in which this can be done is to adjust the height of the step. The exertion level must be chosen so that, while the weaker members of the group must be able to cope with the load, the fitter members must not find it so easy that they are producing performance factors of unity. The test does not permit a comparative assessment to be made between subjects with factors of unity.

In order that the invention may be clearly understood and readily carried into effect, devices in accordance therewith will now be described by way of example, with reference to the accompanying drawings, in which.

There are several ways in which a device can be made to conduct the test as described above but the commercial viability of such a relatively complicated function built into a small package is based on the microprocessor circuits and their associated ancillary circuits which are now available. It will be appreciated that a drawing of the hardware must be of a fairly general system in which almost all of the features (except for the input source) which are peculiar to this invention are hidden in the Read Only Memory (ROM) or Program Memory which carries the set of instructions. It is not possible to give exact details of the program itself without restricting discussion to one particular family of microprocessor chips. It is proposed, therefore, to give a brief description of the hardware and to describe in general terms the main programming techniques required for the present device. This will enable one "skilled in the art" to build a model given this description and the normal technical literature provided by the manufacturer of the particular microprocessor.

(a) HARDWARE

Figure 1:
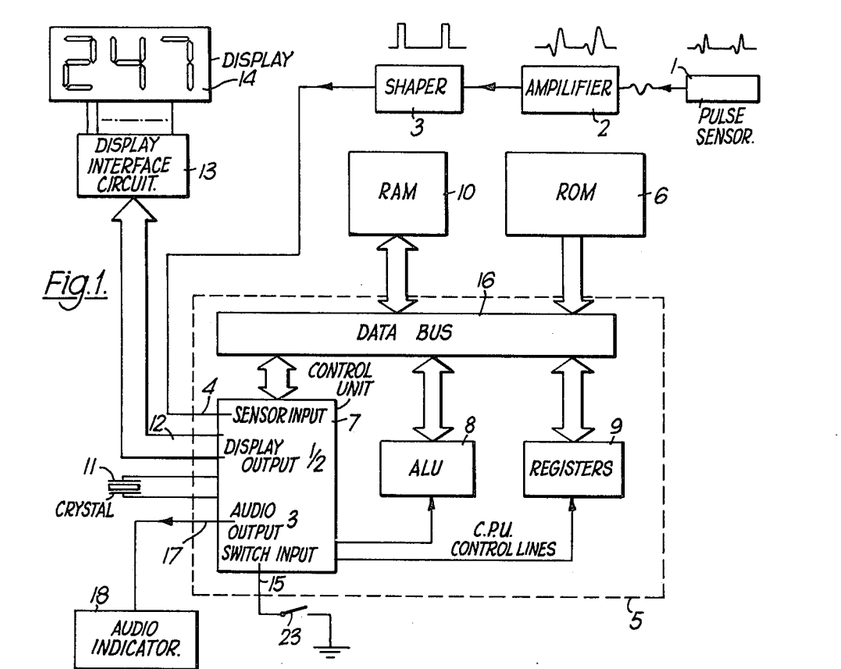
FIG. 1 is a functional block diagram of a performance testing device.
Figure 2:
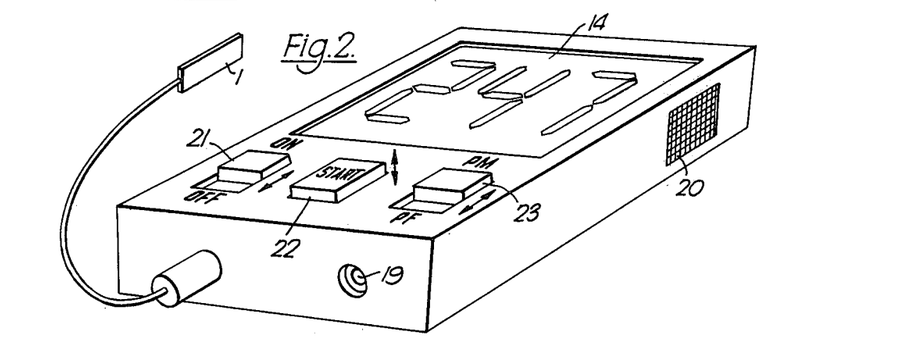
FIG. 2 is a perspective view of a performance testing device.

Referring to FIGS. 1 and 2, a PULSE SENSOR 1 is a piezoelectric displacement sensor operating on the same principle as a phonograph pick-up which is held in contact with the subject at some point where the pulse may readily be detected (e.g., on the thumb side of the wrist for the radial pulse). The sensor is conveniently held in place by an elastic strap or other means. (The construction and use of a modified phonograph cartridge element for the purpose of pulse detection is described by Geddes, L. A. and Hoff, H. E., J. Appl. Physiol., 15, 959–960 (1960). The output level from a sensor of this type is typically 1–3 mV with an effective source impedance of the order of Megohms. The high impedance level demands careful screening of the lead connecting the sensor to an AMPLIFIER 2 which is required to have a suitably high input impedance and sufficient gain to produce an output level of 3–15 volts (depending on the type of microprocessor used). This specification is readily met with an integrated circuit amplifier. The additional frequency response limiting components are made such that there is a rapid cut-off in the region of a few hundred Hz which is ample to pass the pulse signals while avoiding unwanted oscillations. The function of a SHAPER 3 (which may for example be a Schmitt trigger) is to convert the amplified pulse waveform into a rectangular pulse suitable for the input of any microprocessor. (This component may not be required in every case as some of the microprocessors available have inputs designed to accept untreated waveforms).

The CENTRAL PROCESSOR UNIT (CPU) 5 contains the functions enclosed by the dashed line in FIG. 1 which are a CONTROL UNIT 7, an ARITHMETIC LOGIC UNIT (ALU) 8 and REGISTERS 9. All transfers between these functions and the other blocks are via a DATA BUS 16 which is a set of parallel lines (4, 8, 12, or 16 in number depending on the microprocessor—most likely 8 in this application). The broad paths in the diagram indicate these parallel lines—the arrow heads indicating way or ways the signals pass, e.g., a Read Only Memory ROM 6 only provides instructions to the bus whereas a Random Access Memory RAM 10 can exchange data in both directions with the bus. The complicated timing mechanism for routing the signals between the function blocks is contained within the control unit which contains a timing oscillator which requires one external component—usually a QUARTZ CRYSTAL 11 as shown here. (In some cases an inductor, capacitor or resistor may be used instead but a considerable reduction in timing accuracy results). The instructions received by the CPU from the ROM are executed in the CPU or in the CPU in conjunction with the ALU. The REGISTERS are data storage locations for intermediate storage during the execution of instructions and for certain other purposes in the CPU such as counting the program steps. The main temporary store, however, is the RAM in which, for instance, the measured pulse rates $R_1$, $R_2$ and $R_3$ are stored in separate locations pending their use in the computation of the Performance Factor. At appropriate stages in the program the CPU is instructed to examine the voltage at one of the inputs and to JUMP or BRANCH to some specified point in the program according to the condition of the input. When it is required to display data the ROM instructs the transfer of the appropriate data from the RAM locations to the appropriate OUTPUT LINES 12. Usually with an 8-bit microprocessor the data is stored in the RAM in HEXADECIMAL (HEX) form, and, since the display will be in decimal form familiar to users it is necessary to convert the HEX data into BINARY CODED DECIMAL (BCD) form. This conversion can be done by standard sets of instructions programmed into the ROM. At the output from the CPU the BCD data has to be converted into the code required for a 7-segment display and this is the function of a DISPLAY INTERFACE CIRCUIT 13 immediately adjacent to a DISPLAY 14. This extra circuit is included because a standard circuit of this type is the most usual means of interfacing the microprocessor with the display. It is quite feasible, however, to generate the 7-segment coded data within the microprocessor and leave out the interface circuit. It is also possible to obtain individual display digits each one of which has a BCD 7-segment converter integral with it. These could be connected directly to 4-bit groups of the output lines. Whether or not an interface circuit is used in any particular case depends on the number of outputs available, the number of display digits, the ROM capacity available and the type of display.

Switched inputs are used to direct the branching of the program to choose alternative sub-routines in the ROM. The present example shows one such SWITCH INPUT 15 which is used to effect the change from the full Performance Factor measurement program to the simple repeated pulse measurement mode of operation. It is assumed here that the microprocessor has its inputs normally high. In this case all that is required to change the state of the input is a switch between the input and earth (zero volts). A PULSE SENSOR INPUT 4 is of the same type and the polarity of the pulse applied to this input must be arranged to lower the input to earth potential.

It is assumed that the DISPLAY 14 and its DISPLAY INTERFACE CIRCUIT 13 contain between them means of providing the required current and/or voltage requirements of the display elements. The outputs of the microprocessor provide voltage levels of zero volts and the operating voltage of the microprocessor (5-15 V depending on type) but the amount of the current which can be drawn without affecting the microprocessor is very small and in general it will be necessary for provision to be made in the circuitry associated with the display itself. The main types of display are as follows: Light Emitting Diode (LED), liquid crystal and discharge tube. The LED requires relatively high current at low voltage, the liquid crystal requires a low AC voltage and practically no current and the discharge tube requires voltages substantially higher than that of the microprocessor itself. All of these types of display are used in electronic calculators operating from 5-9 V, however, and this has resulted in readily available circuits (both integrated circuits and discrete component sub-assemblies) suitable for the present application.

An AUDIO INDICATOR OUTPUT 18 is a desirable additional feature not essential to the main invention. The object of this component is to provide an audible signal of the step up and step down timing. In the program described below, an AUDIO OUTPUT 17 used for this purpose may be driven alternately high and low at approximate 1 mS intervals by the microprocessor thereby providing an output which can directly drive a high impedance acoustic transducer of the type used in alarm watches. The outlet grill for an internally mounted device of this type is shown in FIG. 2, 20. Alternatively an ear-piece could be used to provide the audio signal. The convenience of deriving the audio frequency source from the microprocessor itself does not preclude the less elegant approach of providing a simple (i.e., non-oscillating) output from the microprocessor and using it to switch any conventional oscillator, buzzer or other acoustic generator.

The only items appearing in FIG. 2 which are not shown in FIG. 1 are: a POWER ON/OFF switch 21, a START BUTTON 22 and a BATTERY RECHARGING SOCKET 19. The device is powered by internal batteries most probably of the rechargeable type used in calculators and similar circuitry will be included for recharging them from an external charger of standard type. This circuitry can be arranged so that (again like most calculators) the device can be operated when plugged into the charger even when the batteries are depleted, without waiting for them to recharge.

How many actual integrated circuit packages are involved in making up the CPU, ROM and RAM combination is variable. Some of the more complex microprocessors have one or more packages for the CPU alone and each of the ROM and RAM may have one or more packages. There are currently available "single chip microprocessors" (e.g., INTEL 8048, 8748, 8021 and 8049) each of which have all three main functions in the one package. The ROM capacity of these devices is such that it is perfectly feasible to accommodate the program for the present device (even with one or two alternative sub-routines in the ROM) on a single chip microprocessor. For reasons of cost (depending on the volume of production) it could well be preferable to have the CPU and RAM on one chip (e.g., the INTEL 8035) with a separate ROM circuit. If a separate ROM is used, "latches" may be required to interface it with the CPU. This is a standard technique and exact details may be obtained from the microprocessor manufacturer.

It is thought also that the function of Program Memory fulfilled by the ROM in the present example might in due course be better performed (with much greater capacity) by Magnetic Bubble Domain Memory or Charge-Coupled Device circuits with associated power supply and address interface circuitry.

(b) PROGRAM

Figure 3:
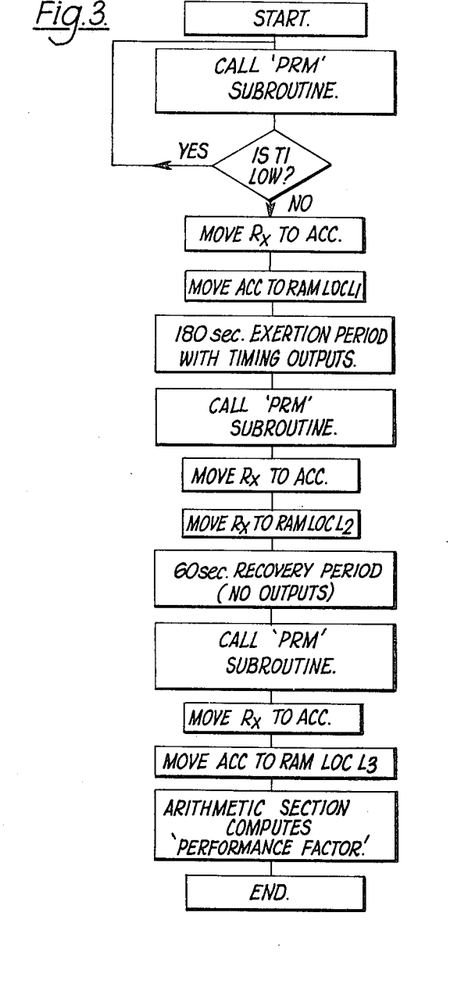
FIGS. 3, 4, 5, 5A and 8 are flow charts.

FIG. 3 is a block diagram of the type of program required. The general programming principles used in the various blocks are described below. Two pulse measuring subroutines are described. The start button initiates the "PRM" subroutine at the end of which the CPU is instructed to examine the switch input (referred to as 'TI' here) and, according to the condition of this input, either proceed to the next stage of the program (if the switch is open) or return to the start of the subroutine (which in this example is also the start of the program). If the switch is closed the device continues to repeat the 'PRM' subroutine and never proceeds to the later stages of the program at all, hence providing the simple pulse measurement mode of operation.

In the present example the 'PRM' subroutine is the only subroutine used. A "subroutine" is a section of the stored program written in a way which permits it to be recalled at various stages of the program. The most obvious way of using the same routine more than once is to repeat the instructions for the subroutine wherever they are required in the program. (With most microprocessors the ROM capacity could well be made to permit this rather basic approach in the present example, but the ROM capacity wasted in this way could be put to much better use in providing alternative subroutines). To call up a subroutine at any desired point in the program two provisions have to be made. (1) Having directed the CPU to jump out of the main program to the location of the start of the subroutine it is necessary to store the position in the main program where this jump instruction is located so that when, at the end of the subroutine, it is desired to direct the CPU to jump back to the main program it can be provided with the address of the ROM location at which it should re-enter the main program. In the more sophisticated microprocessors (e.g., the INTEL 48 series) it is merely necessary to "call" the subroutine giving its start location and to have the subroutine end with the instruction "return". The microprocessor stores the address of the call instruction in a special register and returns the CPU to the next instruction after the completion of the subroutine. To achieve the correct reinstatement of the main program without a special instruction requires the assignment of a register to store the location of the point at which the subroutine was called and the modification of this location (incrementing it by the appropriate number of actual machine instructions) in such a way that at the end of the subroutine the CPU is directed into the ROM at the next instruction after the call instruction. (An instruction may require more than one basic machine instructions and this must be taken into account in the incrementing process). (2) The data resulting from the subroutine must be moved or "stored out" from the subroutine registers to a different RAM location every time the subroutine is used if it is not to be lost when the subroutine is reused. Hence the instructions MOVE $R_x$ to $L_1$, $L_2$, $L_3$ ensure that each measured pulse rate is stored in a separate RAM location for subsequent use in the arithmetic routine to compute the Performance Factor.

PULSE RATE MEASUREMENT ('PRM') SUBROUTINE (Method 1)

A pulse rate measurement ('PRM') subroutine measures the pulse rate per minute (the human range is 40–250 p/m) by starting a timer on the receipt of one pulse at the input and stopping it on the arrival of the following pulse.

The arrival of the first pulse is sensed by a "search loop", the CPU is instructed to examine the sensor input (referred to as 'TO' here) and jump if the input indicates the presence of a pulse (i.e., is low in the present example). If there is no pulse present the CPU proceeds to the next instruction which instructs it to jump back to the previous instruction. The device therefore remains in this two instruction "search loop" until a pulse is detected whereupon the jump instruction causes the CPU to skip the "jump back" instruction and proceed to start the timing procedure. This is achieved by "looping". A register is loaded with data—a number of maximum value (in an 8-bit microprocessor) $FF_{16}$ equivalent to 256 in decimal. The CPU is then instructed to "decrement" the contents of this register or vice versa, move the result to the accumulator (the main temporary register of the microprocessor through which most of the instructions have to operate) and jump if this value in the accumulator is not zero, back to the decrement instruction. The instruction beyond the 'jump if not zero' is not reached until the accumulator becomes zero which only results after the loop has been executed 256 times. Thus the following routine:

---
Load Register $R_y$ with $FF_{16}$

→ Move (contents of) register $R_y$ to Accumulator
      Decrement (contents of) Accumulator
      Move (contents of) Accumulator to $R_y$
   — Jump if Accumulator not zero

--- results in a delay corresponding to the load time of the register plus 256 times the execution time of the next three instructions. Each instruction takes typically 1 or 2 machine cycle times (although some microprocessors do have some instructions with more cycle times) and, depending on the crystal (or other timing device) used as the external timing component, cycle times for microprocessors likely to be used for this application will lie in the range 1–10 microseconds ($\mu$s). The delay caused by the above routine could be made a few milliseconds (ms) in any particular case by suitable adjustment of the number loaded into $R_y$ initially. A further means of adjustment is a "no operation" instruction which simply delays by 1 (or in some cases more) machine cycles and this instruction is used to make small adjustments to delays. The extension to a delay significantly longer than the maximum time achieved with the maximum number in one register ($FF_{16}$ in this case) is achieved by "nesting" loops as follows:

---
Load Register $R_{y+1}$ with $FC_{16}$ (say)

→ Load Register $R_y$ with $FF_{16}$ (say)

→ Move (contents of) Register $R_y$ to Accumulator
       Decrement Accumulator
       Move (contents of) Accumulator to $R_y$
    — Jump if Accumulator not zero
       Move (contents of) $R_{y+1}$ to Accumulator
       Decrement Accumulator
       Move (contents of) Accumulator to $R_{y+1}$
  — Jump if Accumulator not zero

---

Delays of several minutes or longer are readily generated by repeated application of this "nesting" principle.

It should be noted that the steps of the above routine are the most basic and may be used with any microprocessor. Almost all microprocessors have some special instructions which reduce the number of instructions required to implement these very common operations, e.g., most microprocessors have instructions for incrementing or decrementing the contents of a working register without the need to transfer it to the accumulator. Some of the better microprocessors (e.g., the INTEL series already mentioned) have instructions which decrement the contents of an assigned register and jump if the contents are zero—greatly reducing the number of instructions required for nested loops.

Figure 4:
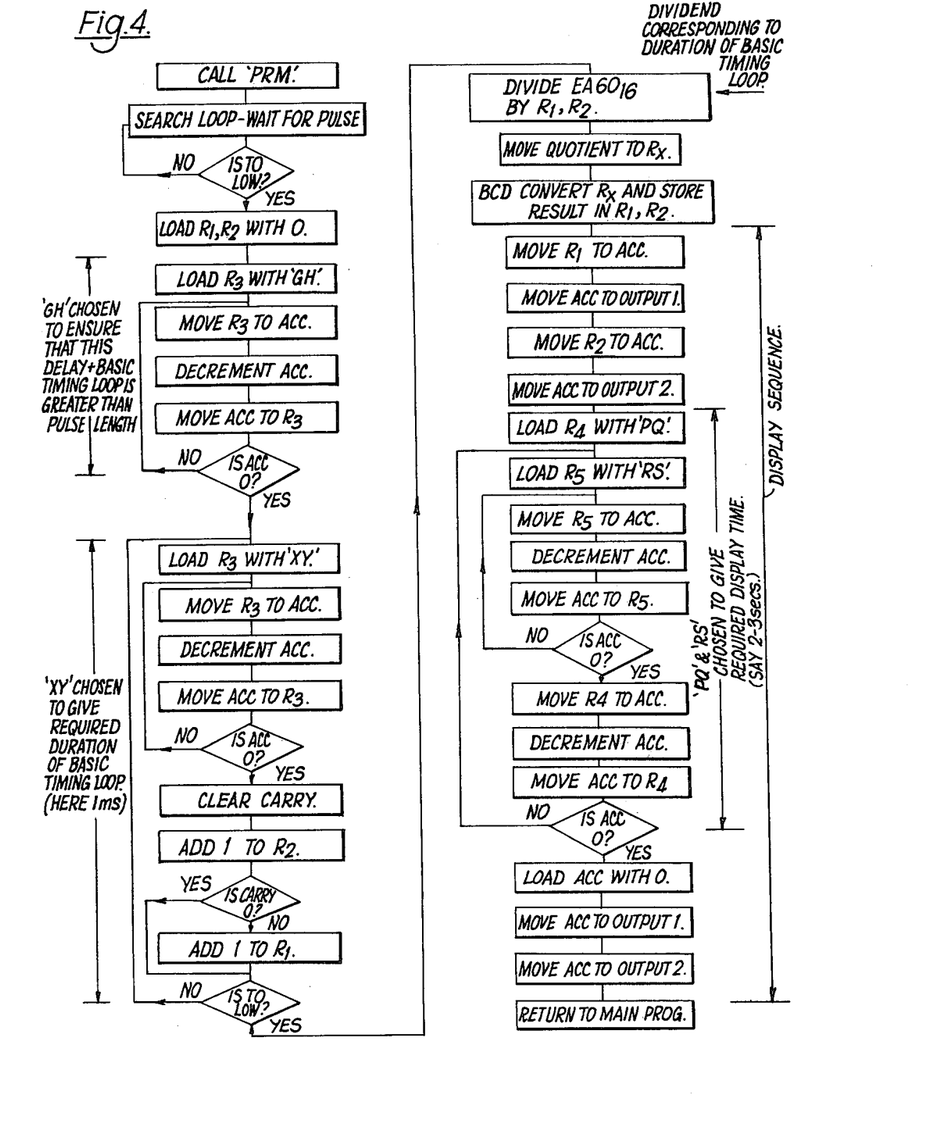

FIG. 4 is a flow chart of a subroutine incorporating the above looping techniques for the measurement of pulse rate per minute. The basic timing loop in this example is chosen as 1 millisecond (which would result in an accuracy of about $\frac{1}{2}\%$). Every time this loop is traversed the input is examined for the presence of the next pulse and if none is present the CPU is sent back to the beginning of the loop. The number of passes through the loop is counted by incrementing a register (previously set to zero) each time so that when the input finally indicates the presence of the next pulse this register contains the number of times the loop delay has to be multiplied to give the time between successive pulses. Provision has to be made to allow the count (which could be as large as $1500_{10}$ for for an abnormally low pulse rate) to overflow the one register (maximum capacity $256_{10}$) into a second register. This is done using the 'carry' mechanism which all microprocessors have, although the exact instructions for its use differ from one microprocessor to another.

In order that the pulse following that which has initiated the counting process is not "missed" by the instruction which examines the appropriate input on each pass through the timing loop, the pulse length (set by the amplifier 2 and shaper 3 in FIG. 1) must be slightly greater than the timing interval. The satisfaction of this requirement, however, does permit the possibility that, if the initial sensing which starts the count occurs very soon after the leading edge of the pulse, the next sensing operation may detect the trailing edge of the same pulse and stop the count after only one pass through the timing loop. This may be prevented by means of an extra delay loop inserted before the start of the first timing loop (i.e., immediately after the first pulse is sensed). This extra delay must be large enough that when added to the normal timing loop delay a time delay greater than the pulse length is achieved. This ensures that, regardless of the point on the pulse that the detection takes place, the delay before the first subsequent sensing of the input is long enough to make it impossible for any point on the same pulse to be detected. All sensing operations after this occur at intervals of the timing loop delay which has been chosen to be shorter than the pulse duration to ensure detection of the next pulse. The timing error which is introduced by this additional delay may be made as small as the accuracy with which the pulse length is determined by the circuitry (amplifier 2 and shaper 3 in FIG. 1) will allow. It should be borne in mind in this context that there is an inherent error of up to one loop delay time in this counting technique. This will be much larger than the error due to the extra delay introduced. The overall accuracy may be improved by shortening the timing loop delay with attendant modification of the pulse length. The general principle is that the timing loop delay is shorter than the pulse length and the timing loop delay plus the extra delay is longer than the pulse length and the difference in each case is as small as the component tolerances will allow.

In FIG. 4 the extra delay and the timing loop delay are shown as being determined by register loads of "GH" and "XY" respectively. The exact values of these numbers depend on the particular microprocessor and crystal (or other external timing component) used. Typically the extra delay might be between 10 and 70% of the timing loop delay.

The result of this counting operation is then divided into the appropriate number to yield the pulse rate per minute ($60,000_{10}$ for a loop delay of 1 ms). This division is done using one of a number of standard algorithms to be found in standard textbooks on computer architecture but which may be better obtained from the manufacturer of the microprocessor being used. Microprocessor manufacturers publish standard routines for arithmetic and these give the instruction sequences which are most economical in terms of ROM space for the instruction set of their particular microprocessor.

The result of this division (regardless of the basic timing loop delay chosen) is limited by physiological considerations to a value which cannot exceed $256_{10}$ ($FF_{16}$) and which can therefore be stored in a single register ($R_x$ in FIG. 4). After completion of the subroutine the contents of this register are moved to a RAM location external to the subroutine so that they are not lost when the subroutine is re-called to measure further pulse rates.

The arithmetic logic algorithms for binary arithmetic are more economical than those for BCD arithmetic algorithms (although both are available). The general forms of the algorithms are available in the standard text-books but it is easier to use the routines available from the microprocessor manufacturer for the microprocessor being used. The arithmetic will be carried out in Hexadecimal (Hex) on an 8-bit microprocessor and the answer (which must always be less than 250 for a human pulse rate) will be contained in one 8-bit BYTE storable in one RAM location or register. The Hex to BCD routine converts this into a series of 3 separate digit codes each of 4 bits. The simplest embodiment of the device would use individual display digits each with its own individual BCD-7 segment decoder integrated on the chip. The output information is simply moved from the memory location or register (perhaps via the accumulator) to the output lines. In this case two outputs would be required each with 8 lines and 4 of these would be free for other use. In most microprocessors information moved to the output in 'latched' at the output lines—i.e., it remains there until cancelled usually by the movement to the lines of zeros. In this case therefore the BCD converted pulse rate (stored in two registers would be moved to the outputs, a delay loop of the required duration for the display (say 2.5 to 3 secs) would be generated using nested loops as described above and then zeros would be moved to the outputs. This would result in zeros being displayed in between the pulse rates which could be rather expensive in power consumption. An improvement would be to use the "blanking" input which all such displays have. This is an input which when driven low turns off the whole display and if an extra line is driven from the microprocessor (e.g., 3 of the 4 spare lines) for each digit this may be used to good effect to turn off the display entirely except for the pulse rate and performance factor displays. To limit consumption further these extra lines could be driven in such a way that the elements of the display are not "on" continuously during the display times, but are driven on and off at such a rate that the human eye does not perceive the non-continuous nature of the display (although some reduction in overall brightness will be visible if the "duty cycle" is low. This is only one stage removed from the "strobing" technique described below.

Alternatives to this simplest approach (for example only) are:

(1) The use of standard routines to convert the BCD to 7-segment code for each digit within the microprocessor would remove the need for the separate decoders. This doubles the number of output lines required for each digit but with 3 digits only, many microprocessors would still have an adequate number of lines.

(2) The digits could be 'strobed' either with BCD to 7-segment conversion on the microprocessor or in an interface circuit, the 7-segments of the 3 digits being connected in parallel and one additional line being provided to the back plane of each digit. The output data is then fed to only one output and thence to all the digits in parallel but the back plane line of only the appropriate digit is driven. Thus the digits are supplied with data in turn—the appearance of a static display being dependent on the inability of the human eye to detect the separate illumination of the digits provided the strobing is carried out at a fast enough speed (about 1 KHz or faster).

(3) The alternating voltage required for a liquid crystal display may readily be generated within the microprocessor following BCD to 7-segment conversion so this very low current consumption type of display may be connected direct to the microprocessor without the need for the interface circuitry provided for in the general description of the hardware. Liquid crystal displays consume so little current that they may be left on continuously in this application.

This technique described in the above section for detecting the pulses by instructing the CPU to examine the appropriate input at certain specific stages in the routine is called "polling" and has been described because it can be used with all microprocessors and is quite adequate for the present application. It is not intended to preclude the use of "interrupts" where these are available and suitable. (An interrupt mechanism is one wherein following a special instruction the CPU will automatically examine a special input (and take appropriate branching action) during the execution of every subsequent instruction (of whatever type). The exact nature of the interrupt mechanism varies from microprocessor to microprocessor and it may or may not be better than polling in any particular case. If used, care must be taken to see that, following an interrupt the mechanism is not "re-enabled" until sufficient time has elapsed for the interrupting pulse to have passed so that two interrupts are not caused by the one pulse.

The most efficient use of the ROM capacity—particularly in a microprocessor with a good "call" procedure for subroutines may demand the making of quite small sections of the program proper subroutines e.g., only one division routine need be included for use wherever required—likewise the hex-BCD routine. It is anticipated that such provisions will be made here. To describe in general terms the programming techniques used and include the possible minor subroutines would be extremely confusing, however, and hence in the above description the only section which is made a subroutine is the one which we wish to be able to recall externally. This does not preclude the use of further subroutines if desired.

PULSE RATE MEASUREMENT ('PRM') SUBROUTINE (Method 2)

An alternative and simpler, although less accurate method of measuring the pulse rate per minute is to count the number of pulses occuring in a specified time interval (say 15 seconds) and scale this number to determine the pulse rate per minute. This may be particularly easily achieved by a microprocessor which has a built-in counter facility and will be described in relation to the INTEL 8748 and 8048 single chip microprocessors. Following an instruction to start counting the CPU counts high to low transitions occuring at one particular input. The count is stored in a special register. At 15 second delay is generated using nested loops at the end of which the instruction is given to stop counting. The stored count is moved to the accumulator and scaled to give the rate per minute. For a 15 sec. interval this is particularly easy since multiplication by 4 simply involves shifting one digit to the left twice. This is achieved by a single instruction for each shift and, since the pulse rate cannot be greater than 256, the maximum value per 8-bit byte, the carry digit need not even be considered. The resulting number representing the pulse rate is then moved to register $R_x$ for subsequent removal by the storing out instructions in the main program.

If this approach is to be employed where no counter facility of the above type is available, the pulse sensing and counting routines must be made to record voltage changes between pulses in order to avoid counting the same pulse twice while not sensing so infrequently that pulses are missed. This problem does not occur with the microprocessors whose action is described above because the counter is actuated by a change in voltage of the input (in one particular direction) not the presence of a voltage.

Apart from being less accurate as a means of measuring a constant pulse rate this method is less attractive than the method shown in FIG. 3, for the important reason that pulse rates $R_2$ and $R_3$ are changing—this being the whole point of the test—and what the method just described measures is the average pulse rate over the counting period. If the period is shortened to reduce the error due to this then the error due to the counting process is increased. In consequence, although this method does more accurately by electronic means what is done manually in the test at present it falls short of the considerable advantage offered by the method of FIG. 3 which (by a process which is inherently more accurate even for a constant pulse rate) permits the pulse rate to be measured virtually instantaneously.

180 sec EXERTION PERIOD TIMING

Figure 5:
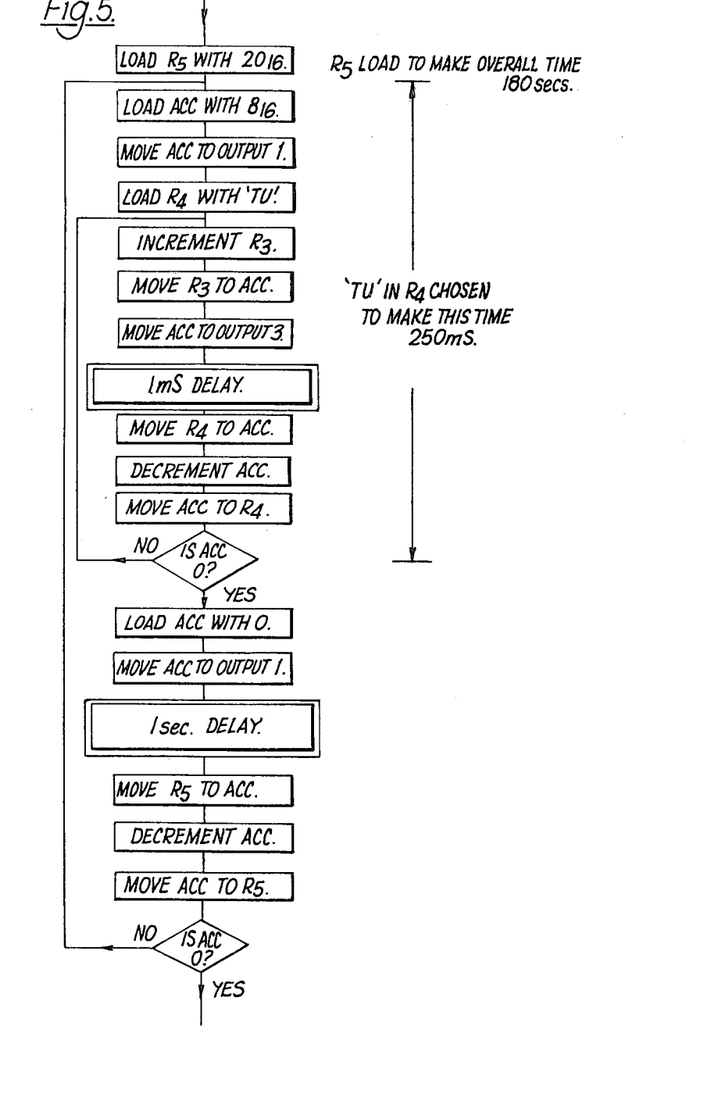

The flow chart in FIG. 5 shows the type of program subsection required for the 180 sec exertion period with display elements ("1s" for example) flashing for 0.25 sec every 1.25 secs to indicate "step up" and "step down" timing with another output alternating between high and low every 1 mS during the 0.25 sec periods to drive an acoustic transducer at approximately 500 Hz.

The two main time delays used in this section are a 1 mS delay and a 1 sec delay. These are shown in the boxes with the double frames and they are generated by looping techniques as described above.

Incrementing the Register $R_y$ and moving it to the output port for the audio transducer every 1 mS causes its Least Significant Bit (LSB) to alternate between high and low.

The exact numbers to be loaded into the registers used to control the looping $Y_{y-1}$, $R_{y-2}$, $R_{y-3}$ are determined by the instruction execution times and quartz crystal frequency for the microprocessor. All microprocessors have some sort of "no op" facility which can be used to "trim" the delay within the loops.

The minimum unit of adjustment which limits the maximum accuracy is one machine cycle time for the microprocessor. This has been described above and for microprocessors of the type likely to be used for this application will be in the range 1-10 $\mu$s. This is well within the required accuracy.

60 sec RECOVERY PERIOD TIMING

A flow chart need not be given for this part of the program since no outputs are required during this period. A nested loop routine as previously described is used—typically 3 loops will be sufficient.

ARITHMETIC ROUTINES FOR PERFORMANCE FACTOR COMPUTATION

All the arithmetic routines required may be achieved by combination of the three basic processes of ADDITION, SHIFTING (sometimes called ROTATION) and COMPLEMENTATION.

All microprocessors have an ADD instruction with some facility for CARRY of the overflow bit (although this latter is implemented in different ways). COMPLEMENTATION makes all the 1's change to 0's and vice versa. Formation of the complement followed by adding one results in a number which when added to another number produces the difference between the original number and the number to which the complement plus one was added. This operation is the process by which subtraction is effected in most microprocessors (some have a specific subtract instruction but this is by no means general).

Multiplication is achieved by successive addition and shifting right of the multiplier. The carry bit produced by the right shift determines whether or not the addition takes place on that shift or not. (If the carry bit is a one the addition takes place—if zero it does not).

Division is achieved by successive shifting left of the dividend followed by subtraction. If the subtraction produces a carry bit, the quotient (or partial quotient) is increased by one and the result of the subtraction becomes the new dividend (or partial dividend). If the subtraction does not produce a carry bit then a zero is placed in the corresponding position in the quotient or partial quotient and the dividend is restored to its value before the subtraction (either by recalling it from a storage register or by adding back the number that was subtracted (the divisor)).

The number of iterations in the multiplication and division routines is that appropriate to the number of bits in the multiplier and divisor respectively. (There are variations in the detail of the routines caused by the exact nature of certain instructions).

Figure 5A:
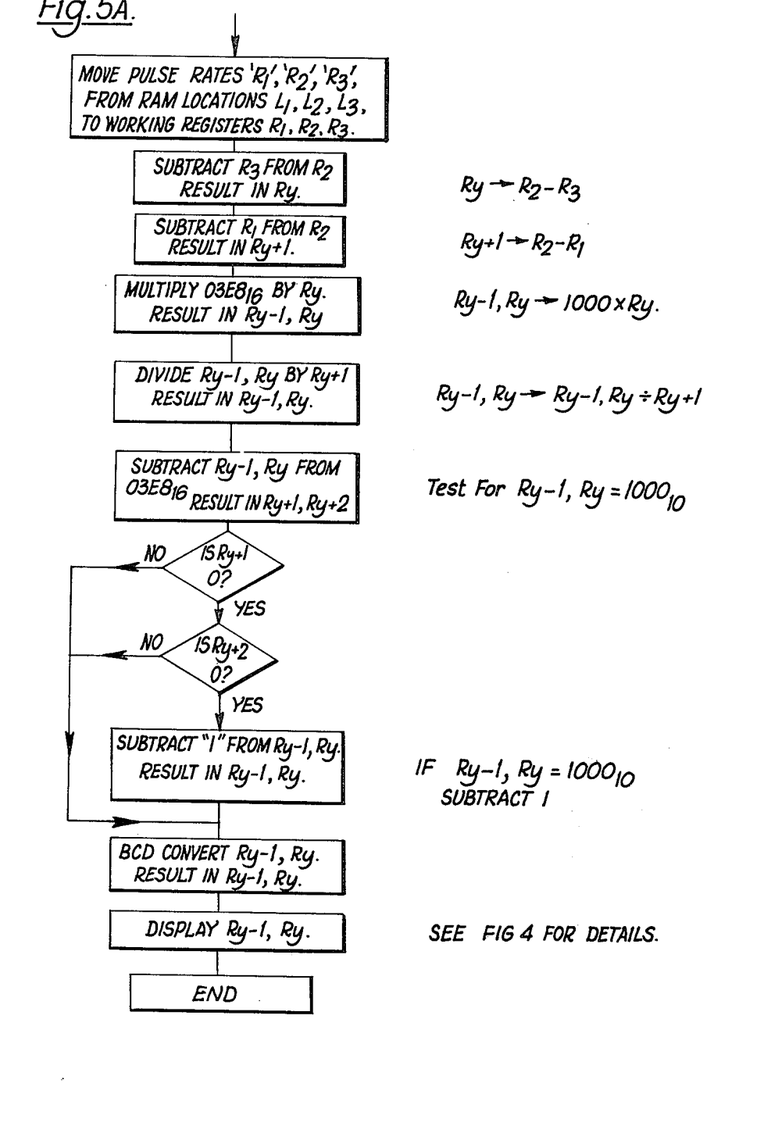

There are several possible ways of computing the Performance Factor (PF) in the chosen example—for example only: (see FIG. 5a):

Subtract $R_3$ from $R_2$ and store the result in $R_y$
Subtract $R_1$ from $R_2$ and store the result in $R_{y+1}$
Multiply $R_y$ by 1000 and store the result in $R_{y-1}$,
$R_y$ ($1000_{10}$ equals $03E8_{16}$)
Divide $R_{y-1}$, $R_y$ by $R_{y+1}$ and store back to $R_{y-1}$, $R_y$.
$R_2 > R_3$ and $R_2 > R_1$ and $R_1 < R_3$ so that the above arithmetic produces no negative numbers and no fractions and the final answer for PF will lie between 0 and $03E7_{16}$. (In the absolute limit PF may equal one more than this number, viz. $03E8_{16}$ in which case it must be reduced by one before the BCD conversion routine is entered. This may be achieved in a number of ways, e.g., Subtract the computed PF from $03E8_{16}$ (i.e., $1000_{10}$)
Jump if not zero to BCD conversion routine
Subtract 1 from the computed PF
BCD subroutine If it is desired to eliminate the case where the PF is greater than $1000_{10}$ (which can only occur if the test has not been carried out properly in that the initial pulse rate is not a true rest pulse rate such as will occur if the test is conducted immediately after a period of intense activity), this may be achieved by examining the carry digit after subtraction of the PF from $03E8_{16}$ and jumping to a separate routine if the carry bit is set. The separate routine could cause a non-standard set of segments to be displayed indicating a fault in the conduct of the test. It is not anticipated that this will be a normal feature of the basic device but rather a desirable addition.

Having computed the PF and made sure that it cannot exceed $03E7_{16}$ ($999_{10}$) BCD conversion is required before the PF is moved to the output lines. Standard BCD conversion routines are based on the following principle:

Repeated subtraction of $64_{16}$ ($100_{10}$) from the PF are carried out until the remainder is less than $64_{16}$ (the carry digit is again used to determine this limit). The count of the number of subtractions which were possible is stored as the "hundreds" digit. The process is repeated, this time repeatedly subtracting $A_{16}$ ($10_{10}$) from the remainder from the first subtraction sequence and the number of possible subtractions is stored as the "tens" digit. The remainder after this is the "units" digit. (Since the conversion from hexadecimal to BCD is a very common requirement, microprocessors often have special instructions to facilitate this conversion. The above principle, however, may be used on any microprocessor without dependence on special instructions).

As in the section covering the 'PRM' subroutine, the simplest way of realising the invention is to deliver each of the 4-bit codes to a separate output line simultaneously, time a suitable delay (say 3–5 secs in this case) and then deliver zeros to the output lines to cancel the display. The display of the computed PF is the last operation of the whole program and there is, in principle, no reason why the display cannot be left illuminated until the program is re-run or until the device is switched off. It is most likely, however, that, unless a very low current display (e.g., liquid crystal) is being employed, it will be considered desirable to prevent unnecessary battery drain by limiting the duration.

A desirable additional feature which could be incorporated is that one extra line could be driven from the microprocessor for each digit which would blank the digit, providing an alternative method of turning off the display after the desired time while leaving the PF data still on the output lines. A separate push button to the display could then be provided which would permit the manual recall of the last measured PF.

All the alternatives such as strobing, conversion from BCD to 7-segment code in the microprocessor, etc., are usuable at this stage as well.

It is proposed now to look (in somewhat less detail) at some of the extensions which it may be desirable to incorporate.

PERFORMANCE FACTOR IMPROVEMENT

Given the same three measured pulse rates $R_1$, $R_2$ and $R_3$, it is conceivable that they can be combined in a number of ways other than the above. The alternatives fall into two general categories:

(a) Better formulae to measure the same sort of factor as above, i.e., assessment of general state of health rather than absolute capacity. For example, in this category, assuming that the rise in pulse rate during exertion is approximately linear with time whereas the fall during the recovery period is likely to be exponential, it could be argued that the formula:

$$PF = (\log_e R_2 - \log_e R_3)/(R_2 - R_1)$$

is a better indicator for comparative purposes. (This would require a rather longer ROM program for not much improvement—proved as yet— which is why it is not included in the basic program).

(b) Performance factors designed to provide different criteria of assessment. For example, instead of normalising out natural differences in capacity with which the subject may be endowed (which would normally be disregarded by a doctor in assessing the general state of health), a formula could be devised which is designed to incorporate some assessment of such natural endowment. This could be achieved to some extent using the formula:

$$(100/R_1) \times (R_2 - R_3)/(R_2 - R_1)$$

The multiplication of the previous factor by $(100/R_1)$ reflecting the fact that a low rest pulse rate is usually associated with a large "stroke/-volume index" meaning that the heart can pump a relatively large amount of blood per stroke. This latter does not in itself indicate a good state of health but, taken in conjunction with a high recovery rate would normally tend to indicate that the subject was potentially capable of performing mechanical work efficiently. It is envisaged that some formula of this type might be used, say, to make comparative assessments of a group of teenagers to assess their potential for training as competitive athletes.

Another such factor might be $R_1 \times R_3(R_2 - R_1)$ based on the principle that a fit person would have a relatively small value of each of the factors in the formula. It should be noted that, in this case the smaller the value of the factor the better (for all formulae hitherto discussed the reverse has been true). It should also be noted that arrangements would have to be made to decide how the computed factor would be "fitted" into the display using the chosen number of digits (usually but not necessarily 3).

DEVICE EMBODIMENTS OF INCREASED COMPLEXITY

Figure 6:
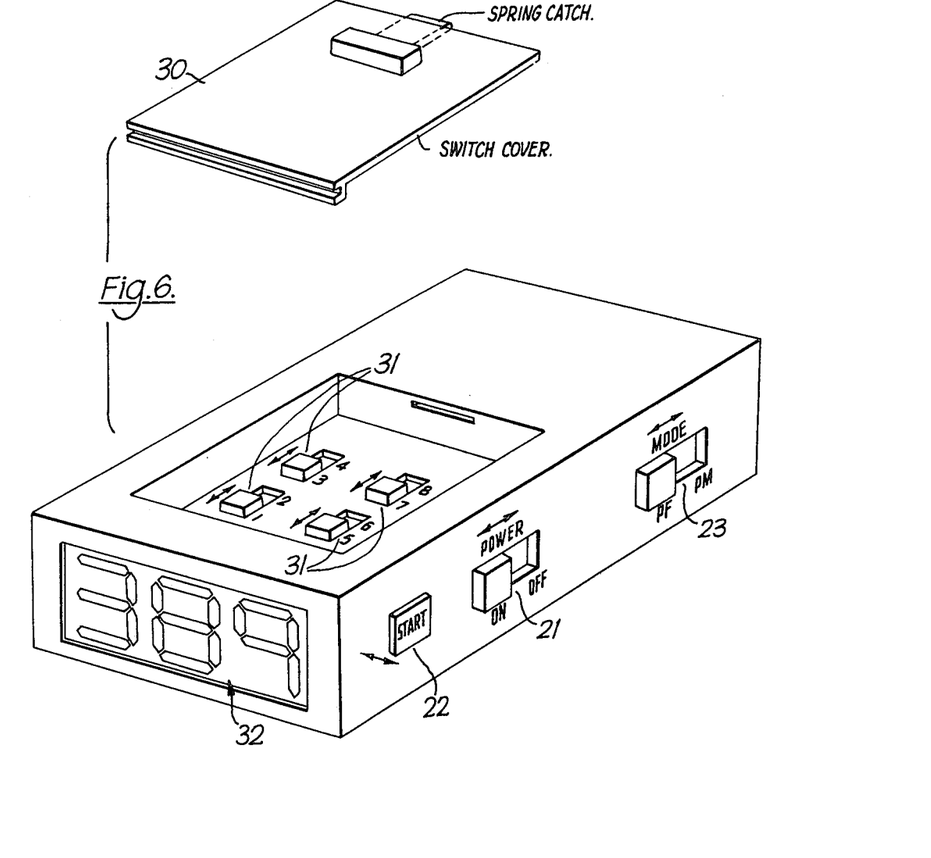
FIGS. 6 and 7 are perspective views of two further performance testing devices.

FIG. 6 shows a device differing only in the respect that there are extra switches 31 shown under an optional removable panel 30 in the outer enclosure. These switches alter the state of input lines (in exactly the same way as that used in the basic device to provide the 'PRM' only mode) which cause the program to branch to alternative subroutines. The ROM capacity even of simple single-chip microprocessors is increasing rapidly and it is realistic to expect that a considerable number of subroutines can be provided giving an even greater number of combinations. The optional removable panel 30 is desirable in the case of a device offering a wide range of alternatives to have the immediate user or subject provided with a device set up for simple use by a supervisor (e.g., doctor or trainer). In this way the simplicity of operation of the basic device is not lost to the user.

The block diagram of the circuit is not repeted here since it is essentially the same as FIG. 1 with the exception that there will be several input lines connected to earth (or to supply voltage as appropriate for the microprocessor being used) each one with a switch.

In relation to the possibility of offering a large number of switchable alternatives, it should be pointed out that most microprocessors have a limited number (e.g., one or two) of testable inputs of the type described so far. Most microprocessors however, have a much larger number of parallel input and output lines arranged as parallel input and output "ports". When used as inputs these lines are read (or sensed) by instructing the transfer of the contents of the port (as an 8-bit pair of Hex digits in the case of an 8-bit microprocessor) to the accumulator and performing the 'AND' or the 'OR' operation on it with an 8-bit number called a 'MASK'. The object of this process is to permit the reading of selected bits from the input port (i.e., determining whether each bit has been wired or switched high or low). This operation of masking is another operation so commonly required that some microprocessors (e.g., the INTEL 8748, 8048 etc.) have special instructions which permit this to be done at the port without the necessity to move the data to the accumulator.

It is not essential that all alternatives contained in the ROM are available in any particular device. It is quite conceivable, particularly as ROM sizes (even those on single-chip microprocessors) increase, that a ROM could contain a large number of possible alternatives all of which, either for reasons of device cost or undesired complexity, it may not be desired to incorporate as switchable alternatives in all devices using this ROM. It is likely that a single ROM may be employed wherein alternatives are contained from which the program for, say, a number of single function devices and a number of devices offer alternative functions. The choice may be made by switches or by printed circuit board interconnections or (most probably) some combination of the two.

The alternatives include changes in stepping rate, duration of exertion period and duration of recovery period. Several different formulae for performance factor computation may be included.

For example only, the configuration in FIG. 6 shows the display on the end to facilitate reading by the user when being worn attached to the breast pocket or hung around the neck on a lanyard. It will be noted that the separate switch to operate the 'PRM' only mode has been retained so that it is not necessary to remove the cover (if fitted) to change to this mode.

The scope of what can be done with careful programming of a suitably large ROM seems to include all the range of program variations foreseeable without losing the simplicity of operation. The following are included as further examples.

USE OF PLUG-IN ROMS

As has already been mentioned one possible embodiment involves the use of a single device containing all of the required functions except the ROM which is separate. It has also been mentioned that in this case latching arrangements of a standard nature (with minor variations for individual types of microprocessor) require to be made in most cases for external ROMs. Such an arrangement offers the possibility of providing several alternative ROMs which can be plugged into a socket to select a given program or set of programs. Some provision would have to be made to ensure that the exposed connections of the ROMs do not acquire static charge during handling. This can be done either by care in handling or by providing a holder which keeps the pins of the ROM integrated circuit electrically connected until they are actually plugged into the socket.

USE OF ELECTRICALLY ALTERABLE OR ELECTRONICALLY PROGRAMMABLE ROM DEVICES

There exist the possibilities of using either as a separate ROM or within a special single chip microprocessor a special type of ROM called an EPROM (Electronically Programmable ROM). As its name suggests this ROM is not permanent but can be altered. The ROM, once programmed, behaves just like the normal ROMs described above i.e., with normally applied microprocessor voltages it is a permanent program memory. It is non-volatile i.e., it is not lost when the power supply to the device is switched off. The top of the microprocessor or ROM package is transparent, however, and if the circuit is exposed to the prescribed level of ultra-violet radiation for a period of some tens of minutes the ROM memory is erased. Using appropriate circuitry which supplies data to the ROM of the type normally stored therein but at a voltage level much higher than the normal operating voltage (e.g., 25 v for a 5 v microprocessor) the EPROM can then be re-programmed. Also available are electrically alterable ROM's (EAROM's) which can be re-programmed by higher than normal voltage pulses.

It is therefore possible to envisage an embodiment wherein the device is in appearance and normal use just like the basic device or the basic device with ROM alternatives but with a special socket so that it may be plugged onto special circuitry called a PROGRAMMER which would be a system containing most of the elements of the device shown in FIG. 1, but with a very much larger program memory perhaps extended by external memory devices e.g., tape cassette, floppy disc, bubble domain memory etc. This programmer can program and reprogram the internal ROM of the performance tester.

THE KEYBOARD PROGRAMMABLE TYPE

Figure 7:
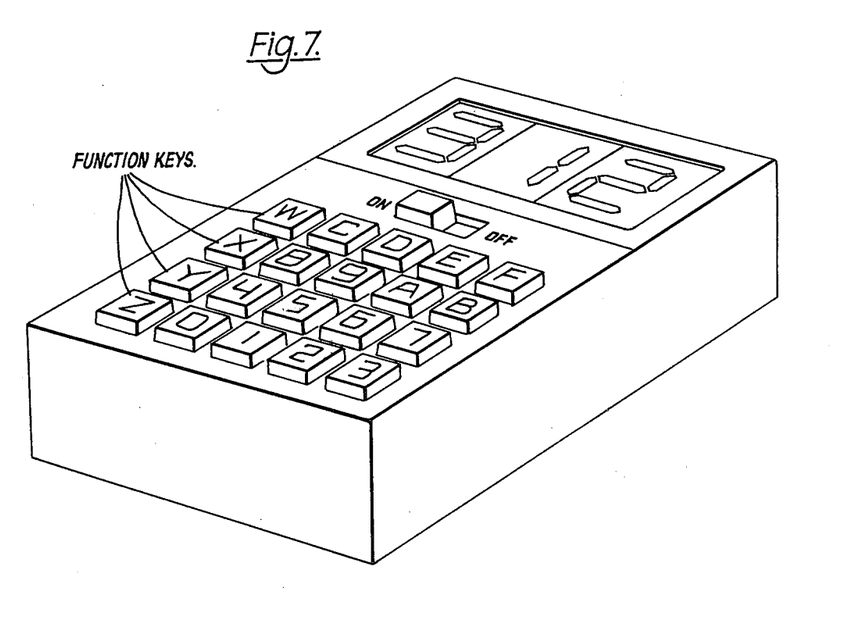

FIG. 7 shows an embodiment wherein the various parameters of the test can be varied by the user. This would allow, for example, the stepping rate, exertion time and recovery time to be set to any desired values decided by the user—not merely selected from a set of alternatives. The alternative formulae for the Performance Factor would still have to be written into the ROM as alternative subroutines, however, which means that the other side of the device shown would have to be provided with switches as shown in FIG. 6.

The keys marked 0–9 and A–F are the conventional Hexadecimal keys. The keys marked W, X, Y and Z are function keys or keys which would direct the microprocessor to the appropriate locations in the RAM for the information put in by the keys following the function key. For example, instead of having the values of the data loaded into the registers determining the times in the timing cycles as part of the program memory (ROM), these would be keyed into special RAM locations and the program would instruct the CPU to move the data into the working registers at the appropriate point in the program. Unlike the switches used in all the previous embodiments described which are of a type which hold their position once set, the keys of a keyboard are only depressed momentarily. The keyboard is continually scanned at a sufficiently high rate that no keystrokes can be missed and the data read in is stored in order of arrival in assigned memory locations. The technique of scanning the keyboard is standard and may be done under the control of the instructions of the program memory. However, there exist special keyboard and display interface circuits for many microprocessors (e.g., the Intel 8279 for use with the 8748 and 8048 microprocessors). These circuits contain standard routines for scanning the keyboard and also usually for strobing the display (which latter may or may not be required in the present case) which operate compatibly with the CPU in the microprocessor.

"PACK" TYPE OF TEST

The PACK test (which in modified form is used by the Ministry of Defence for testing the fitness of personnel in the Armed Forces) is a test of similar overall concept to the Harvard Step Test, except for the important respect that it improves on the single measurement nature of this latter test by taking three measurements of pulse rate. It differs from the proposed test which is the subject of the main description within this specification in that all three rates are measured during the recovery period. The test is described in "Principles of Human Physiology" by E. H. Starling and C. A. Lovatt Evans. The stepping form of exertion is carried out in an exactly similar fashion to the tests described above and in the proposed device the rate would be signalled in the same manner. The pulses are counted from 1 min to 1 min 30 sec, again from 2 min to 2 min 30 sec and again from 3 min to 3 min 30 sec after the exertion has ceased. The Pack Index is then computed from the following formula:

$$\text{Pack Index} = \frac{(\text{exertion time in secs}) \times 100}{2 \times (\text{sum of three pulse counts})}$$

which, since the pulse counts are taken over 30 sec periods, is equivalent to:

$$\text{Pack Index} = \frac{(\text{exertion time in secs}) \times 100}{(\text{sum of three pulse rates per min})}$$

A good value of Pack Index is around 100.

The Ministry does not actually use the "Index" as such but simply computes the sum of the three pulse counts (each taken over 30 sec.) and uses this in conjunction with tables and other tests. (It uses a 5 min exertion period with 30, 18 inch (45.7 mm) steps/min).

The current method of conducting the Pack Test acknowledges the non-instantaneous nature of manual pulse measurement by counting the pulse over 30 sec intervals thereby removing a possible source of inconsistency due to leaving to the individual tester the decision of how long an interval to count over. As has already been discussed in relation to Methods 1 and 2 for pulse rate measurement, the method (1) based on timing the interval between two successive pulses is a more accurate method of determining pulse rate than the method based on counting pulses over a given time interval (which, in addition to being less accurate, merely gives the mean pulse rate over the period. Thus for the most accurate method of conducting a test involving the use of three measured rates during the recovery period the best technique to be employed would be Method 1 and the second of the two Pack Formulae above would be used. However, since the pulse counting method is universally accepted as the Pack Test and some tables are available to relate measured performance to age, sex etc., it is proposed to describe here an embodiment of the present invention designed to conduct the Pack Test electronically in a manner completely compatible with all measurements taken manually which are based on this test.

Figure 8:
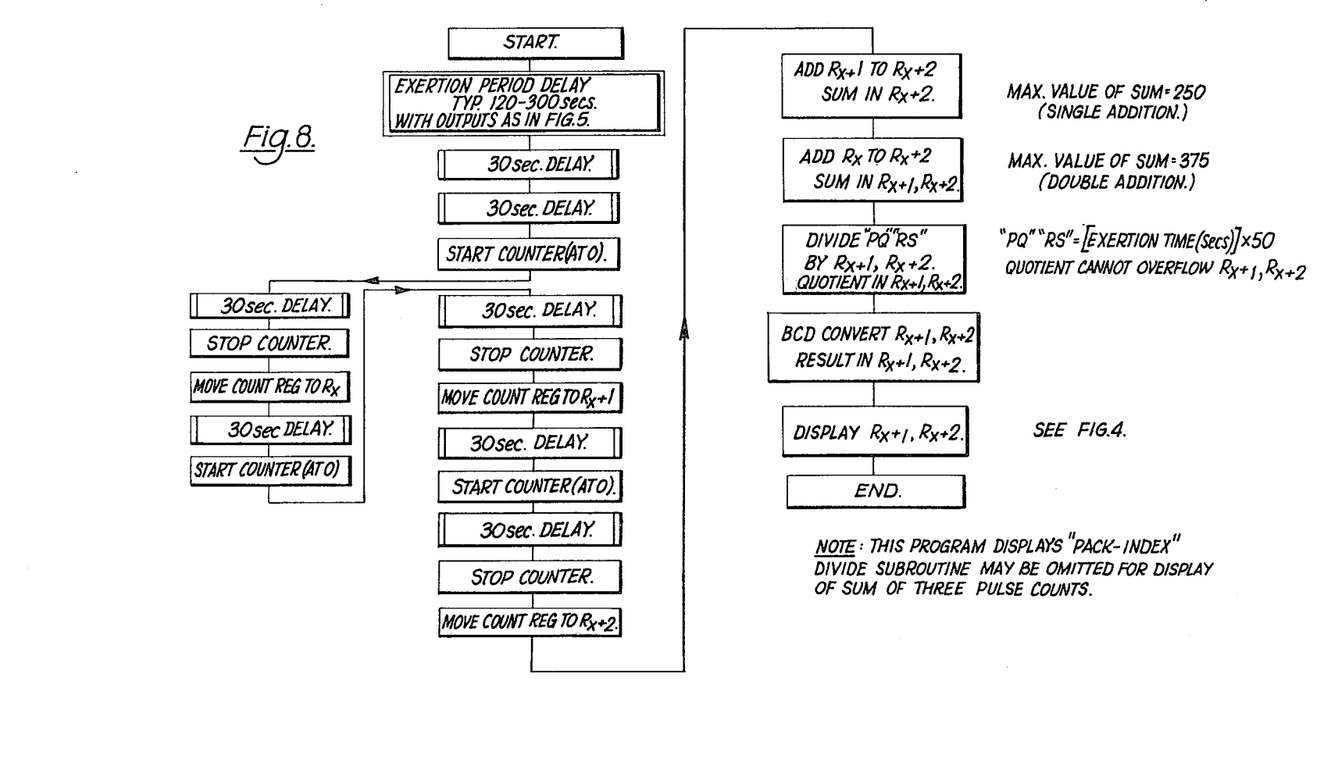

FIG. 8 shows a block flow chart wherein the detail of the blocks is not given since they have either been described in detail above or are standard arithmetic routines. The flow chart is based on a delay unit of 30 secs which can be recalled both for the counting intervals and for the delays between these. As is indicated on the flow chart, the division routine to produce the "Pack Index" may be omitted to display the sum of the three counts.

Obvious alternatives are to display first the sum followed by the Pack Index or to provide a switched alternative which can be set before the test is commenced. The display of the BCD converted information may be effected as shown in the last column of the flow chart in FIG. 4. (It should be stressed here, perhaps, that as this method is based on method 2 of pulse measurement it is dependent on the use of a microprocessor (such as the INTEL 8048 or 8748 already cited) which has provision for counting pulses).

To offer the alternative of a more accurate method of conducting the test by the more accurate method 1 of pulse measurement in the most compatible form for the existing data, an instantaneous pulse measurement would be taken at 1.25, 2.25 and 3.25 minutes after exertion ceases. It may also be worth noting that the additional ROM capacity required to increase the number of repetitions of any subroutine already in the ROM is very small indeed. Thus it would be very easy to extend either of the above routines to take more measurements during the recovery cycle.

COMBINED PERFORMANCE FACTOR AND PACK TYPE TEST

The advantages of both categories may be combined to produce a test with the information from three recovery measurements used in conjunction with the rest pulse rate and the rate immediately following exertion. The latter is less important (slightly) because the information is present in the three recovery rates to allow this to be computed from the time intervals. The inclusion of the rest rate offers the additional advantage of making some allowance for individual differences thereby making the test much less dependent on the use of tables to interpret the result.

To take the simplest possible example of how the two tests might be combined, consider the following:

The pulse rate is measured before the exertion period ($R_1$), immediately after the exertion period ($R_2$) and at intervals of, say 1, 2 and 3 minutes after exertion has ceased (it is assumed that the more accurate Method 1 is being used to measure instantaneous pulse rate) ($R_3$, $R_4$ and $R_5$).

The Performance Factor is computed as before:

$$\frac{(R_2 - R_3)}{(R_2 - R_1)}$$

this is then multiplied by the Pack Index (× 10):

$$\frac{(\text{Exertion time (secs)}) \times 1000}{(R_3 + R_4 + R_5)}$$

This will provide a 'Combined Factor' of which a good value would be something approaching 1000.

The main description covered in some detail the steps necessary to ensure that the Hexadecimal number which is the factor to be displayed does not overflow the BCD routine appropriate to the number of digits in the display. Similar conditions apply here. To avoid going into too much detail on a specific example, a general (if slightly less cost-effective) means of obviating trouble of this sort is to extend the BCD routine to include "thousands" and provide one more digit than the three (which have in any case only been chosen as a likely example). The output lines would then have provision for 4 BCD digits (each requiring 4 bits). Thus by ensuring that both the BCD conversion routine and the display can cope with the largest possible or greater number, it may not be necessary to explain in detail how the display is made most economically to accommodate the result.

I claim:

1. An electronic physiological performance testing device comprising a portable housing and, in the housing:
    means for receiving signals representing instantaneous pulse rates of a subject;
    first time period establishing means for establishing a first predetermined period of time between first and second ones of said signals;
    second time period establishing means for establishing a second predetermined period of time between the second one and a third one of said signals;
    store means connected to the signal receiving means and responsive to said first and second time period establishing means for storing three pulse rates $R_1$, $R_2$, and $R_3$ at instants separated in time by said predetermined time periods where $R_1$ is the subject's pulse rate at rest, $R_2$ is the elevated pulse rate resulting from the performance a specified amount of work by the subject, and $R_3$ is the recovery pulse rate at a specified time after ceasing said performance of the specified amount of work;
    computing means connected to receive the three stored pulse rates $R_1$, $R_2$ and $R_3$ and deriving therefrom a performance factor which is a predetermined function thereof; and
    display means for displaying the performance factor.

2. A device according to claim 1 provided with means for generating a periodic humanly-perceptible signal throughout the time interval between the storage of the first and second signals, whereby a person under test may perceive the rate at which specific exertion is to be undertaken.

3. A device according to claim 2 in which said generating means comprises an integral audio output device.

4. A device according to claim 1, including a timing device and a control unit, and in which:
    said signal receiving means comprises an amplifier connected to receive the input pulse rate signal;
    said control unit being connected to the output of said amplifier to control routing of the pulse rate signal at intervals controlled by the timing device;
    the store means comprises a random access memory (RAM);

the output of said amplifier being fed by the control unit at said instants to specified RAM locations;

the computing means comprises an arithmetic logic unit (ALU) and a read only memory (ROM);

the ROM being connected to the control unit to instruct the output of data from the RAM to the ALU;

and the display means comprises a numeric display device driven by a display interface circuit which is connected to the control unit to receive a computed performance factor from the ALU.

5. A device according to claim 4 comprising at least one microprocessor having a data bus connected to the control unit, the arithmetic logic unit, the RAM and the ROM.

6. A device according to claim 5, in which the ROM circuit is on one chip and the RAM, arithmetic logic unit, registers and data bus are on a second chip.

7. A device according to claim 4 including means for starting the timing device on receipt of one pulse signal by the control unit and stopping it on receipt of the following pulse signal, whereby the pulse rate is measured.

8. A device according to claim 7 including means for counting the number of pulses received in a time interval determined by the control unit and timing device and means for scaling the number of pulses to determine the pulse rate per minute.

9. A device according to claim 4, comprising a removable panel in the housing beneath which are located a number of switches enabling the program to be changed over to alternative subroutines stored in the ROM.

10. A device according to claim 9 including means for electronically altering the ROM.

11. A device according to claim 1, in which the means for displaying the performance factor also includes means for displaying the stored pulse rates.

12. A device according to claim 1 including means for computing the performance factor as $(R_2-R_3)/(R_2-R_1)$.

13. A device according to claim 1 including means for computing the performance factor as $(\log_e R_2 - \log_e R_3)/(R_2 - R_1)$.

14. A device according to claim 1 including means for computing the performance factor as $(100/R_1)[(R_2-R_3)/(R_2-R_1)]$.

15. A device according to claim 1 where said signal receiving means includes a piezoelectric displacement sensor for sensing the signals representing the instantaneous pulse rates of the subjects.

* * * * *